(12) United States Patent
Tricca

(10) Patent No.: US 6,783,604 B2
(45) Date of Patent: Aug. 31, 2004

(54) SYSTEM AND METHOD FOR CLEANING ALIGNERS

(75) Inventor: Robert E. Tricca, Danville, CA (US)

(73) Assignee: Align Technology, Inc., Santa Clara, CA (US)

(*) Notice: Subject to any disclaimer, the term of this patent is extended or adjusted under 35 U.S.C. 154(b) by 80 days.

(21) Appl. No.: 09/967,626

(22) Filed: Sep. 28, 2001

(65) Prior Publication Data

US 2003/0062062 A1 Apr. 3, 2003

(51) Int. Cl.[7] ............................ B08B 3/12; B08B 7/04
(52) U.S. Cl. ........................ 134/32; 134/33; 134/184; 134/187; 134/188; 422/300
(58) Field of Search .................. 134/169, 184, 134/32, 33, 187, 188; 422/300

(56) References Cited

U.S. PATENT DOCUMENTS

| | | | |
|---|---|---|---|
| 729,536 A | | 6/1903 | Brown |
| 2,231,790 A | * | 2/1941 | Andress .................. 422/300 |
| 2,744,635 A | | 5/1956 | Hiss |
| 3,085,583 A | | 4/1963 | Siek |
| 3,376,878 A | | 4/1968 | Shoemaker |
| 3,821,117 A | | 6/1974 | Breece et al. |
| 3,921,458 A | * | 11/1975 | Homm .................... 134/140 |
| 3,936,385 A | | 2/1976 | Cheng |
| 4,237,912 A | * | 12/1980 | Hill et al. .................. 134/57 R |
| 4,381,285 A | * | 4/1983 | Wittenberg .................. 422/116 |
| 4,721,124 A | | 1/1988 | Tuerkheimer et al. |
| 4,857,224 A | | 8/1989 | Eoga |
| 4,922,939 A | | 5/1990 | Adamczyk |
| 4,986,290 A | | 1/1991 | Oguma et al. |
| 5,421,353 A | | 6/1995 | Jakubowski |
| 5,494,531 A | | 2/1996 | Azuma |
| 5,624,636 A | * | 4/1997 | Schwartz .................... 422/37 |
| 5,690,211 A | | 11/1997 | Jao et al. |
| 5,758,675 A | | 6/1998 | Scheyer |
| 5,950,644 A | | 9/1999 | Brewer |
| 5,975,893 A | | 11/1999 | Chishti et al. |
| 6,213,777 B1 | | 4/2001 | Seitzinger |

\* cited by examiner

Primary Examiner—Alexander Markoff
(74) Attorney, Agent, or Firm—Townsend and Townsend and Crew LLP; Bao Tran, Esq.

(57) ABSTRACT

Apparatus for cleaning removable oral appliances, such as tooth repositioning aligners, comprise a base having a tray for holding the appliance in a bath of cleaning solution. A low-frequency driver is provided in the base for reciprocating the tray about a horizontal or vertical axis to wash the cleaning solution over the appliance. Usually, the apparatus will further comprise a cradle which is mounted to reciprocate about a horizontal axis within the base. The cradle defines a receptacle which removably receives the cleaning tray. The cleaning tray is preferably reciprocated at frequency in the range from 1 Hz to 10 Hz, usually in the range from 2 Hz to 5 Hz.

8 Claims, 5 Drawing Sheets

SYSTEM AND METHOD FOR CLEANING ALIGNERS

BACKGROUND OF THE INVENTION

1. Field of the Invention

The present invention relates generally to the cleaning and hygienic maintenance of oral appliances. More particularly, the present invention relates to the cleaning of removable orthodontic appliances, such as removable tooth repositioning appliances.

A variety of removable orthodontic and other oral appliances have been developed over the years for different purposes. Of particular interest to the present invention, a number of these appliances are formed from clear, translucent, or tooth-colored materials in order to make the appliances "invisible" or at least reduce their visibility during use. Since these appliances are used in the oral environment, however, they are subject to discoloration and contamination from a number of sources. For that reason, as well as for simple oral hygiene, it is necessary to periodically clean and preferably sanitize the appliances prior to replacement by the patient.

A number of cleaning systems have been developed for removable oral appliances over the years. Most common are cleaning systems for removable dentures. Most simply, in the past, patients have cleaned dentures using brushes and toothpaste, as well as other stronger cleaning materials. More advanced cleaning systems for dentures rely on ultrasonic action to enhance the cleaning ability of the cleaning system which is used.

Recently, orthodontic systems comprising multiple "aligners" have been developed and are marketed by Align Technology, Inc., under the tradename Invisalign® System. The aligners are thin-shell polymeric appliances which are shaped to progressively move teeth from an initial configuration to a final desired configuration. The aligners are molded plastic devices formed from polycarbonate and more recently from polyurethane materials. The aligners are intended to be clear and are worn for periods from one to several weeks in each stage of treatment before being replaced by a new aligner.

During the use of any single aligner, it is desirable to clean the aligners once a day. The cleaning, however, must be of a relatively short duration since the aligners are intended to be worn at all times, other than when eating, during toothbrushing, or when the aligner is cleaned. Thus, the possibility of soaking the aligners overnight or for other extended periods is not possible for the aligners of the Invisalign® System.

For these reasons, it would be desirable to provide improved apparatus and methods for cleaning removable oral appliances, such as aligners of the Invisalign® System. It would be further desirable if such apparatus and methods were useful for other removable oral appliances, such as plastic retainers, tooth positioners, and the like. Such apparatus and methods should be able to clean the removable appliances in a very short time, preferably in less than 30 minutes, while providing a high degree of cleaning so that the clear or translucent nature of the appliance is not significantly diminished. The apparatus and methods should of course not leave any residual materials or effect on the appliances which would diminish their intended use or present risk to the patient in any way. Such apparatus and methods should further be convenient to the patient, preferably requiring little effort other than initiating a cleaning cycle, and should be robust and reliable so that the apparatus does not fail, even after repeated uses. At least some of these objectives will be met by the inventions described hereinafter.

2. Description of the Background Art

The Invisalign® System is generally described in U.S. Pat. No. 5,975,893, the full disclosure of which is incorporated herein by reference. Aligners in the Invisalign® System are presently available in both polycarbonate and polyurethane materials. Cleaning of the Invisalign® System aligners has heretofore been preformed by patients on an ad hoc basis, typically using brushes, denture cleaners, and other non-optimized approaches.

Denture cleaning tablets and compositions are described in U.S. Pat. Nos. 3,936,385; 3,821,117; and 4,857,224. Mechanical denture cleaners are described in U.S. Pat. Nos. 729,536; 2,744,635; 3,085,583; 3,376,878; 4,986,290; 4,721,124; 4,922,939; 5,421,353; 5,494,531; 5,690,211; 5,758,675; 5,950,644; and 6,213,777B1.

SUMMARY OF THE INVENTION

According to the present invention an oral appliance cleaning system comprises a base and a tray in the base for holding the appliance in a bath of cleaning solution. A low frequency driver is also provided in the base for reciprocating the tray about an axis to wash the cleaning solution over the appliance. Usually, the axis will be horizontal so that the tray is rocked with its ends reciprocating vertically and alternating upward and downward strokes. Alternatively, the axis could be vertical, with the tray rotated in a reversing, rotational pattern about the vertical axis.

In a preferred embodiment, the low frequency driver comprises a cradle mounted to pivot about a horizontal axis within a cavity in the base. The cradle will have a receptacle for removably receiving the tray which holds the appliance. Thus, the appliance-holding tray can be removed from the apparatus to facilitate washing, placement of the appliance into the tray, filling the tray with cleaning solution, etc. Usually, the tray will have a removable cover so that the tray can be closed prior to placement into the cradle within the base. This is an advantage since it reduces the chance that the cleaning solution will splash from the tray during the cleaning process.

In a specific embodiment, the low-frequency driver further comprises a vertical link attached to one end of the cradle and a reciprocating motor, such as a solenoid or other magnetic driver, attached to the other end of the vertical link. Operation of the motor will reciprocate the vertical link which will in turn rock the cradle. Preferably, the motor will reciprocate at a low frequency in the range from 1 Hz to 10 Hz, preferably in the range from 2 Hz to 5 Hz.

Methods according to the present invention comprise filling a tray with a cleaning solution, placing the appliance in the tray, placing the tray in a cradle, and rocking the cradle at a low frequency, typically in the range from 1 Hz to 10 Hz, preferably in the range from 2 Hz to 5 Hz, to gently but effectively wash the appliance to provide for thorough cleaning and hygiene. Preferably, the tray will be covered prior to initiating rocking of the cradle. More preferably, the cleaning solution comprises a chlorine-based material.

In another aspect of the present invention, an oral appliance cleaning apparatus comprises a base having a cavity, a tray having a removable cover for holding the oral appliance in a cleaning solution, a cradle mounted within the base cavity and having a receptacle for removably receiving the tray, and means in the base for agitating the cradle to clean the oral appliance held within the tray. Preferably, the cradle is mounted in the cavity to pivot about a horizontal axis. More preferably, the agitating means comprises a low-frequency driver for reciprocating the cradle about the horizontal axis at a frequency in the range from 1 Hz to 10 Hz, preferably in the range from 2 Hz to 5 Hz.

DESCRIPTION OF THE SPECIFIC EMBODIMENTS

Figure 1:
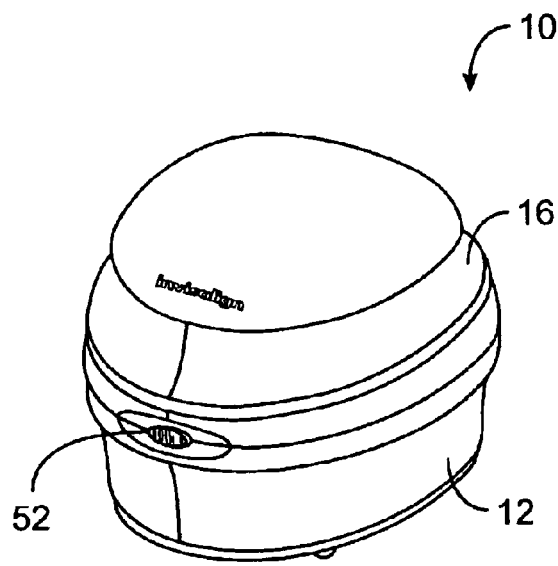
FIG. 1 illustrates a perspective view of apparatus according to the present invention.
Figure 2:
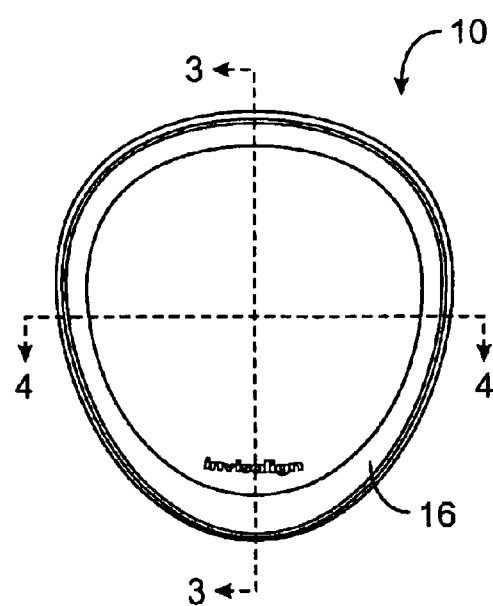
FIG. 2 is a top plan view of the apparatus of FIG. 1.
Figure 3:
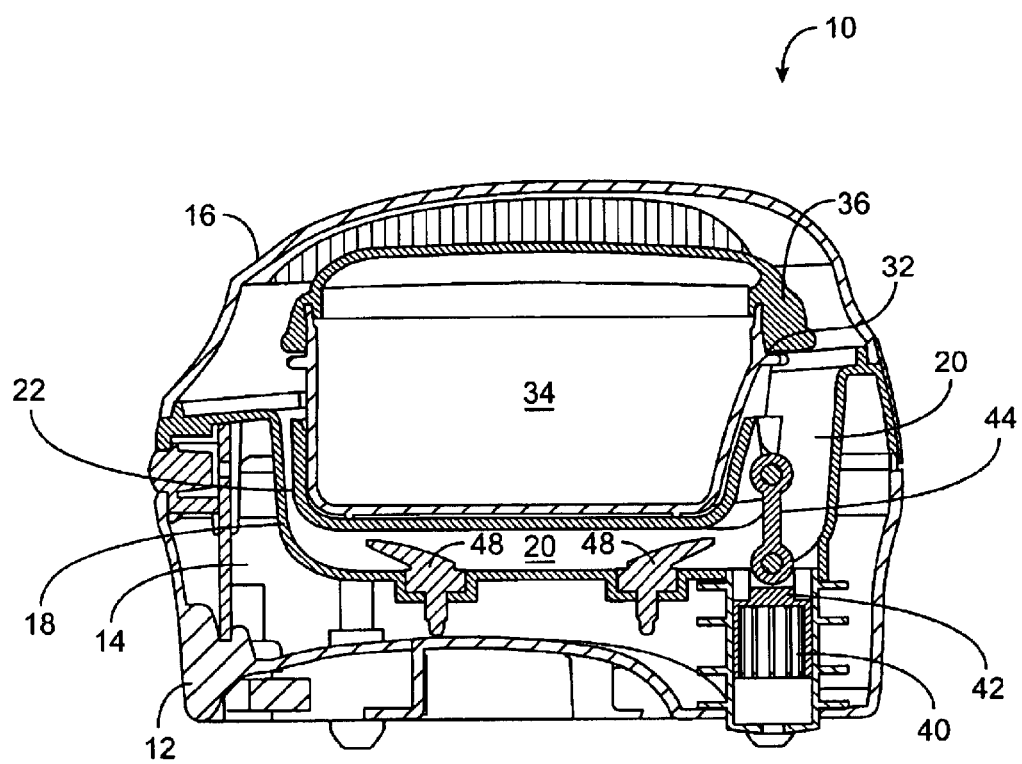
FIG. 3 is a cross-sectional view taken along line 3—3 of FIG. 2.
Figure 4:
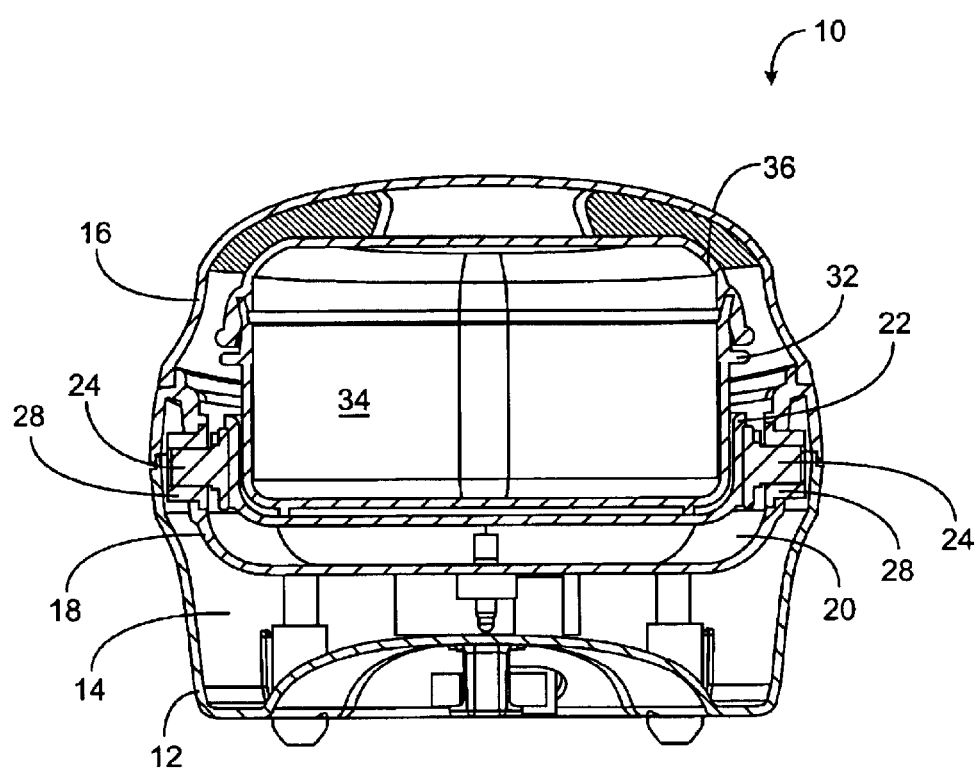
FIG. 4 is a cross-sectional view taken along line 4—4 of FIG. 2.
Figure 5:
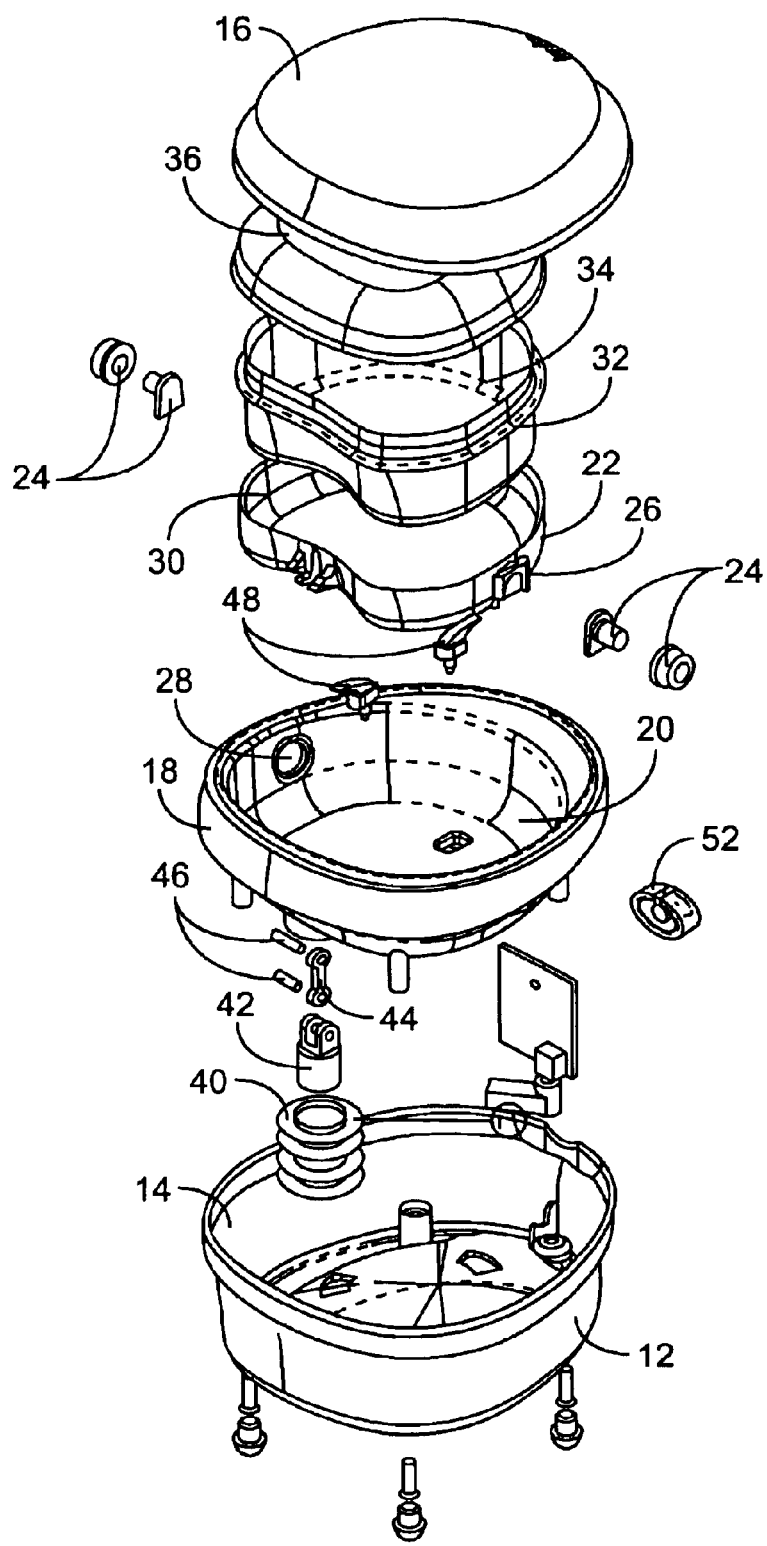
FIG. 5 is an exploded view of the apparatus of FIG. 1.

Referring now to FIGS. 1–5, an oral appliance cleaning apparatus 10 comprises a base 10 having an internal cavity 14 and a removable cover 16. A cavity insert 18 fits within the cavity 14 of base 12 and defines a well 20 which receives a pivotally mounted cradle 22. The cradle 22 is mounted on bearing assemblies 24 which attach to side plates 26 on the tray 22 and to attachment points 28 on the inner surface of the cavity insert 18.

The cradle 22 is thus pivotally mounted within the well 20 of cavity insert 18. The cradle in turn defines a receptacle 30 for removably receiving a tray 32 having an interior 34 for receiving the appliance to be cleaned as well as the cleaning solution. Usually, a cover 36 will be provided so that the interior 34 of the tray may be sealed during the cleaning process. Such sealing is beneficial both to keep the cleaning solution inside the tray where it can clean the appliances, and to prevent spillage of the cleaning solution into the remainder of the appliance and in particular into the appliance base where it could ultimately damage system components.

The oral appliance cleaning apparatus 10 includes a mechanism for reciprocating the cradle 22 relative to the base 12. As described above, the cradle 22 is pivotally attached within the cavity insert 18 so that it may be pivoted or rocked back and forth relative to the horizontal axis defined by the bearing assemblies 24, as best observed in FIG. 4. In the specific embodiment, the apparatus 10 comprises a driver assembly including a motor 40, a piston 42 which is reciprocatably driven by the motor 40, and a link 44 attached at one end to the piston 42 and at the other end to the lower portion of the cradle by cotter pins 46. Dampening bumpers 48 are mounted in the bottom surface of the cavity insert 18 to provide for a controlled, gentle stopping of the cradle as it is reciprocated by the drive assembly, as described in greater detail hereinafter.

Operation of the cleaning apparatus is controlled by an electronic circuit panel 50 and initiated by a single button 52 on the front of the apparatus. A single depression of the button 52 initiates power to the motor 40 which in turn begins reciprocating the cradle 22 at the desired frequency. Timing circuitry is built in to the control panel 50 so that reciprocation of the cradle is terminated at a desired time, preferably from about 5 minutes to 30 minutes after initiation, usually being about 15 to 20 minutes. The control circuitry then initiates an audible signal to tell the user that cleaning is complete. Usually, the control circuitry on the panel will also light a pilot indicator when the unit is in operation.

Figure 6A:
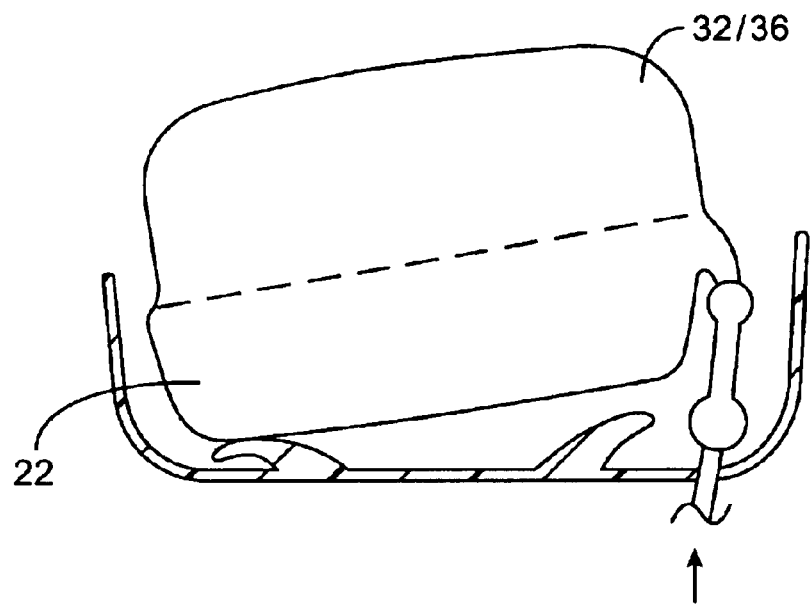
FIGS. 6A and 6B illustrate operation of the apparatus of FIG. 1 to clean appliances according to the method of the present invention.
Figure 6B:
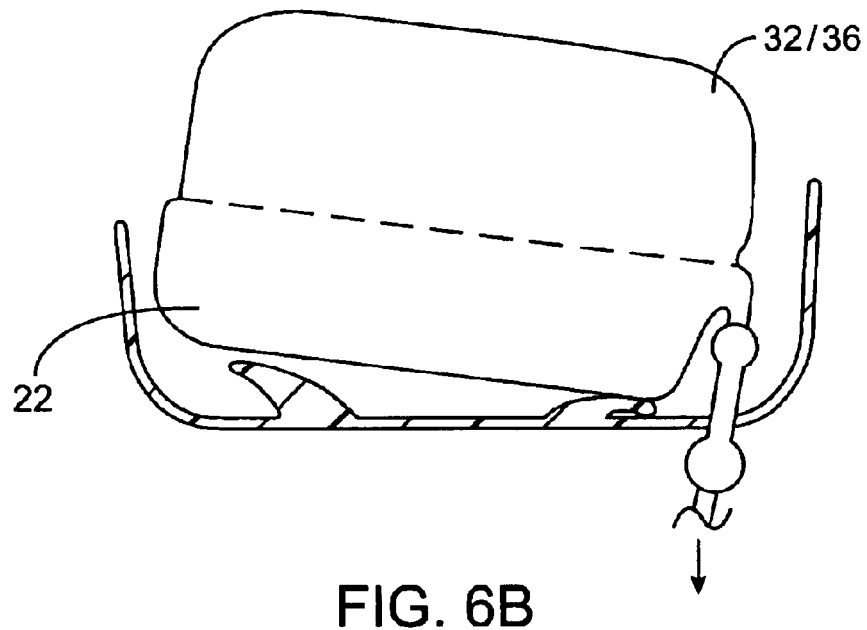

Referring now to FIGS. 6A and 6B, cleaning of an appliance is performed by first removing a tray 32 with cover 36 from the appliance 10. The cover 36 is removed from the tray 32, and cleaning solution introduced into the interior 34 of the tray. Preferably, the cleaning solution will be chlorine-based. More preferably, the cleaning solution will be formed by placing a tablet or dry powder into the tray and adding tap water to form the cleaning solution. Most preferably, the cleaning solution will be formed from sodium dichlorisocyanurate, preferably to provide active chlorine in solution in the range from 10 ppm to 3000 ppm, usually in the range from about 100 ppm to 300 ppm. The cleaning solution will normally be employed at room temperature. After forming the solution, the aligner or other removable appliances are placed in the tray, and the tray 32 recovered with lid 36. The assembly of tray 32 and lid 36 is then placed into the cradle 22, and system operation initiated by pressing button 52. The cradle 22 then rocks back and forth as illustrated in FIGS. 6A and 6B, causing the cleaning solution to gently pass back and forth over the appliance in the tray. It has been found that such a rolling action of the cleaning solution is highly effective in cleaning the aligners, such as the polycarbonate and polyurethane aligners of the Invisalign® System, and reducing or eliminating discoloration. Moreover, the cleaning solution does not significantly affect the mechanical properties of the polycarbonate and polyurethane aligners to any noticeable extent.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An oral appliance cleaning apparatus comprising:
    a base;
    a tray in the base for holding the appliance in a bath of a cleaning solution;
    means comprising an axis for mounting the tray in the base; and
    a driver in the base for reciprocating the tray about the axis to wash the cleaning solution over the appliance at a frequency in the range from 1 Hz to 10 Hz.

2. An apparatus as in claim 1, wherein the low frequency driver comprises:
    a cradle mounted to pivot about a horizontal axis within a cavity in the base, said cradle having a receptacle for removably receiving the tray; and
    a removable cover for the tray.

3. An apparatus as in claim 2, wherein the low frequency driver comprises a vertical link attached at one end to the cradle and a reciprocating motor attached to the other end of the vertical link, wherein operation of the motor reciprocates the vertical link to rock the cradle.

4. A method for cleaning oral appliances, said method comprising:
    providing the apparatus of claim 2;
    filling the tray with a cleaning solution;
    placing the appliance in the tray;
    placing the tray in a cradle; and
    rocking the cradle about the axis at a frequency in the range from 1 Hz to 10 Hz to wash the appliance.

5. A method as in claim 4, further comprising covering the tray and covering the cradle before starting to rock the cradle.

6. A method as in claim 4, wherein filling comprises filling the tray with a chlorine solution.

7. An oral appliance cleaning apparatus comprising:

a base having a cavity;

a tray having a removable cover for holding the oral appliance in a cleaning solution;

a cradle mounted within the base cavity and having a receptacle for removably receiving the tray;

means in the base comprising a horizontal axis for mounting the cradle in the base; and means in the base for pivoting the cradle about the horizontal axis to clean the oral appliance.

8. Apparatus as in claim 7, wherein the pivoting means comprises a low frequency driver for reciprocating the cradle about the horizontal axis at a frequency in the range from 1 Hz to 10 Hz.

* * * * *